US010000536B2

(12) United States Patent
Ostermann et al.

(10) Patent No.: US 10,000,536 B2
(45) Date of Patent: Jun. 19, 2018

(54) METHOD FOR COATING SUBSTRATES WITH AT LEAST ONE MONOLAYER OF SELF-ASSEMBLING PROTEINS

(75) Inventors: Kai Ostermann, Dresden (DE); Leopold Gruner, Dresden (DE); Gerhard Rödel, Karlsfeld (DE)

(73) Assignee: Technische Universität Dresden, Dresden (DE)

( * ) Notice: Subject to any disclaimer, the term of this patent is extended or adjusted under 35 U.S.C. 154(b) by 973 days.

(21) Appl. No.: 14/240,426

(22) PCT Filed: Aug. 24, 2012

(86) PCT No.: PCT/EP2012/066493
§ 371 (c)(1),
(2), (4) Date: May 20, 2014

(87) PCT Pub. No.: WO2013/026919
PCT Pub. Date: Feb. 28, 2013

(65) Prior Publication Data
US 2014/0255712 A1    Sep. 11, 2014

(30) Foreign Application Priority Data

Aug. 24, 2011  (DE) .................. 10 2011 081 524
Dec. 20, 2011  (DE) .................. 10 2011 089 241

(51) Int. Cl.
*C07K 14/37*    (2006.01)
*B05D 3/00*     (2006.01)
(Continued)

(52) U.S. Cl.
CPC .............. *C07K 14/37* (2013.01); *B05D 3/007* (2013.01); *B05D 7/24* (2013.01); *C07K 14/38* (2013.01);
(Continued)

(58) Field of Classification Search
CPC ...................................................... C07K 14/37
(Continued)

(56) References Cited

U.S. PATENT DOCUMENTS

2009/0226887 A1    9/2009  Brisson

FOREIGN PATENT DOCUMENTS

DE   10 2005 051 515 A1    5/2007
EP         1 252 516 B1    10/2002
(Continued)

OTHER PUBLICATIONS

Zhang et al., Adsorption Behavior of Hydrophobin and Hydrophobin/Surfactant Mixtures at the Solid-Solution Interface, Jul. 2011, 27, pp. 10464-10474.*
(Continued)

*Primary Examiner* — Dah-Wei D Yuan
*Assistant Examiner* — Andrew Bowman
(74) *Attorney, Agent, or Firm* — Gudrun E. Huckett

(57) ABSTRACT

The invention relates to methods for coating a substrate with at least one monolayer of self-assembling proteins, using stabilized aqueous solutions with self-assembling proteins, and also to substrates obtainable as a result. Methods for stabilizing solutions with self-assembling proteins, and the stabilized solutions obtainable therefrom, are likewise provided by the invention. According to the coating method, at least one monolayer of a self-assembling protein is produced on a substrate by first providing a stabilized aqueous solution which comprises at least one self-assembling protein. To provide the coating solution, protein units aggregated from an aqueous solution of self-assembling proteins are separated off, and addition of a solution of ionic surfactants and/or of a salt-containing and/or alkaline and/or acidic solution to the protein-containing coating solution generates monomers or oligomers of the self-assembling proteins, and
(Continued)

stabilizes them, the amount of ionic surfactant added being such that only the surface-active part of each active protein monomer or predominant protein oligomer is enveloped by surfactant particles. A substrate surface is then brought into contact with the stabilized, protein-containing solution, thus producing a protein-containing coating on the substrate. The supernatant solution is removed from the coated substrate and/or the coated substrate is dried.

7 Claims, 2 Drawing Sheets

(51) Int. Cl.
  B05D 7/24 (2006.01)
  C07K 17/00 (2006.01)
  C07K 14/38 (2006.01)
  C09D 5/00 (2006.01)
(52) U.S. Cl.
  CPC ............ C07K 17/00 (2013.01); C09D 5/00 (2013.01); *Y10T 428/31725* (2015.04)
(58) Field of Classification Search
  USPC .......................................... 427/384
  See application file for complete search history.

(56) References Cited

FOREIGN PATENT DOCUMENTS

| EP | 1 777 520 A1 | 4/2007 |
| WO | 96/41882 | 12/1996 |
| WO | 01/57066 A2 | 8/2001 |
| WO | 2005/068087 A2 | 7/2005 |

OTHER PUBLICATIONS

Egelseer et al., Genetically Engineered S-Layer Proteins and S-Layer-Specific Heteropolysaccharides as Components of a Versatile Molecular Conctruction Kit for Applications in Nanobiotechnology, 2008, NanoBiotechnology: BioInspired Devices and Materials of the Future, Ch. 4, pp. 55-86.*

Schem M.: Mikrostrukturierung von Lanthanoid-dotierten, Sol-Gel-basierten dünnen Schichten; Disseration; Westfälische Wilhems-Universität Münster, Germany, 2005; pp. 76-79.

Zhang Xiaoli L. et al.: Adsorption behavior of hydrophobin and hydrophobin/surfactant mixtures at the solid/solution interface; Langmuir : The ACS Journal of Surfaces and Colloids; vol. 27, No. 17, pp. 10464-10474 (Jul. 28, 2011); cited in international search report.

Neda Habibi et al.: Self-assembly and recrystallization of bacterial S-layer proteins of Bacillus sphaericus and Bacillus thuringiensis on slicone, mica, quartz crystal supports; 2010 Annual International Conference of the IEEE Engineering in Medicine and Biology Society; Buenos Aires, Argentina , pp. 3739-3742 (Aug. 31, 2010); cited in international search report.

Schuster B. et al.: S-layer-supported lipid membranes; Reviews in Molecular Biology; vol. 74, No. 3, Sep. 2000; pp. 233-254; cited in international search report.

Egelseer E.-M. et al: Genetically engineered S-layer proteins and S-layer specific heteropolysaccharides as components of a versatile molecular constrcution kit for applications in nanobiotechnology; NanioBioTechnology: BioInspired Device and Materials of the Future; Eds. Oded Shoseyov and Ilan Levy; Humana Press Inc. Totowa,NJ , USA; 2008, II, 55-86.

* cited by examiner

METHOD FOR COATING SUBSTRATES WITH AT LEAST ONE MONOLAYER OF SELF-ASSEMBLING PROTEINS

BACKGROUND OF THE INVENTION

The invention concerns methods for coating a substrate with at least one monolayer of self-assembling proteins as well as substrates obtainable thereby. The invention can be employed in chemical industry, biotechnology, sensor technology as well as in medical research.

Self-assembling proteins, like hydrophobins or surface layer proteins (S-layer proteins), have the tendency to undergo in aqueous solutions a quick and uncontrollable aggregate formation (the uncontrolled agglomeration of protein monomers to multimers of the self-assembling proteins) which complicates the preparation of homogeneous layers of the self-assembling proteins on a substrate. With regard to the invention, self-assembling proteins in the following are also simply referred to as "proteins". Self-assembling proteins, by interactions of the protein molecules with each other, form a directed folded structure and association (molecular self-assemblage) and are suitable, by the formation of this extremely ordered structure, for very different applications in nanotechnology.

Generally, the Langmuir Blodgett method, the Langmuir Schäfer technique or the "layer-by-layer" process are used for building homogeneous layers of self-assembling proteins. In these methods, the substrate is submerged in a solution with protein monomers so that a layer of the protein monomers (monolayer) is deposited on the substrate. The layer-by-layer techniques are based exclusively on the utilization of physisorption of the protein monomers on the substrate surface. Hence, it is necessary to use high purity protein monomers. Because self-assembling proteins have a strong tendency to form aggregates, a long-term storage and use of already prepared protein solutions is not possible. Furthermore, coating of hardly accessible surfaces of the substrate (for example, pores of a substrate) is limited because hardly accessible sites on the substrate, such as for example pores, may become closed off by protein monomers that aggregate in uncontrolled fashion so that further monomers cannot penetrate into pores anymore.

DE 10 2005 051515 A1 discloses methods for coating surfaces with defined fusion hydrophobins. In this context, an aqueous solution having a pH value of ≥4 is contacted with a surface and the solvent is subsequently removed. Other additives, such as for example non-ionic surfactants and/or metal ions, may be added to the hydrophobin solution. The process permits however no controlled deposition of protein layers.

Moreover, processes are known for stabilizing solutions of monomers of self-assembling proteins. For example, a process is known where protein aggregates are dissolved by addition of trifluoro acetic acid (TFA) without damaging the proteins. In view of environmental regulations and the very corrosive properties of TFA, this method is suitable only to a very limited extent for industrial applications.

Furthermore, WO 01/57066 A2 discloses a process where the disulfide bonds within a hydrophobin are cleaved by addition of a strongly denaturing agent, like guanidine hydrochloride, so that the folded structure of the hydrophobin is dissolved. The renewed formation of disulfide bonds in the hydrophobin solution is avoided by addition of suitable agents for forming protective sulfhydryl groups so that the thus generated hydrophobin monomer-containing solutions are stable. For coating a substrate surface with self-assembling protein monomers, the removal of the protective group is then necessary which is effected by addition of an oxidizing agent.

WO 96/41882 A1 discloses hydrophobin assemblage at oil-water interphases. Furthermore, EP 1 252 516 A1 and WO 2005/068087 A1 disclose the immobilization of hydrophobins by means of thermal sample preparation or by shifting the pH value into the acidic range. However, both processes provide no information about the number and homogeneity of the generated hydrophobin layers, for which reason they cannot be used in an application in sensor technology or biomedicine.

SUMMARY OF THE INVENTION

It is the object of the invention to provide a method that enables coating of substrates with at least one monolayer of self-assembling proteins as well as solutions required for this purpose.

According to the invention, the object is solved by a method for coating a substrate with at least one monolayer of self-assembling proteins with the following steps:
  i. providing a protein-containing coating solution,
  ii. contacting the surface of the substrate with the protein-containing solution,
  iii. removing the supernatant solution from the coated substrate and/or drying the coated substrate.

For providing the protein-containing coating solution, aggregated protein units are separated from an aqueous solution of self-assembling proteins such that preferably monomers or oligomers of self-assembling proteins remain in the solution.

Monomers or oligomers of the self-assembling proteins are generated and stabilized in the protein-containing coating solution by subsequent addition of a solution of ionic surfactants and/or a salt-containing and/or alkaline and/or acidic solution. In this context, so much ionic surfactant is added that only the surface-active part of each active protein monomer or predominant protein oligomer is enveloped by surfactant particles.

In aqueous solutions, self-assembling proteins have the tendency to aggregate and form aggregates with more than 10 protein units. With these aggregates a controlled deposition of defined protein layers is not possible. Therefore, it is important that these aggregates are separated and that preferably monomers and oligomers of the self-assembling proteins remain in the separated solution.

The separation occurs advantageously by centrifugation with a centrifugal acceleration of at least 5000×g, preferably 10,000 to 50,000×g, for a period of time of at least 5 minutes, preferably 15-60 min, at a temperature of −10° C. to 40° C., preferably at 0-10° C.

Monomers are the smallest indivisible protein units of a self-assembling protein. Oligomers according to the invention are assembled structures of self-assembling proteins with a size of maximally 10 protein monomers.

For formation and stabilization of monomers of the assembling proteins, ionic surfactants are added to the solution after separation of the protein aggregates such that only the surface-active part of each active protein monomer is enveloped by surfactant particles. With such a coating solution the deposition of protein monolayers on substrates becomes possible without pretreatment. A protein monolayer is a flat structure of surface-assembled protein units, preferably protein monomers, with the layer thickness of a protein monomer.

For formation and stabilization of oligomers of the assembling proteins, a solution of ionic surfactant and/or a salt-containing and/or alkaline and/or an acidic solution is added to the solution after separation of the protein aggregates. In this context, ionic surfactants are added in such amounts that only the surface-active part of each active predominant protein oligomer is enveloped by surfactant particles.

The formation of predominant protein oligomers with compensation of protein charges is promoted by the addition of salts, bases or acids. Upon incubation of the protein-containing solution with the added solution, the counter ions form with the proteins contained in the aqueous solution a coordinative bond so that a protein-counter ion complex is formed. The controlled formation of oligomers of the proteins (assembled structures) is triggered and stabilized by the formation of the protein-counter ion complex.

After separation of the protein aggregates, the concentration of the self-assembling proteins in the aqueous solution amounts to at least 5 ng/µl, preferably at least 50, particularly preferred at least 90 ng/µl. The aqueous solution of the self-assembling proteins has preferably a pH value of 7 to 9.5. In this context, the solution is preferably a buffered solution.

As self-assembling proteins, hydrophobins and/or surface layer proteins (S-layer proteins) and/or recombinant fusion proteins with at least two domains, wherein at least one domain is a self-assembling protein domain and one domain is a functional domain, are used.

Preferred hydrophobins are hydrophobins of the class I, preferably Ccg2 from *Neurospora crassa*, or hydrophobins of the class II, preferably HFBI or HFBII from *Trichoderma reesei*. Preferred S-layer proteins are SbsC from *Bacillus stearothermophilus*, S13240 from *Bacillus stearothermophilus* or SsIA from *Sporosarcina ureae*.

The invention is especially advantageously suitable for functionalized self-assembling proteins because the accessibility of the functionalization can be guaranteed by the coating of the functionalized self-assembling protein according to the invention. It is advantageously possible to carry out coating of the substrate in such a way that the functionalization is provided on the side of the protein-containing coating that is facing away from the substrate.

The self-assembling protein is preferably a chemically modified or a recombinant fusion protein, i.e., a protein which is produced by genetically modified organisms. By fusion of the genes of two or more protein domains that do not exist in this combination in nature and that are usually connected by flexible linker structures (linker peptides) with each other, the recombinant fusion protein is available by expression of the fused gene. A recombinant fusion protein used in the invention encompasses at least two domains, wherein at least one domain is a self-assembling protein domain (selected preferably from the aforementioned self-assembling proteins) and one domain is a functional domain. Preferred functional domains are fluorescent protein domains, catalytic domains or protein domains with enzyme activity.

A solution with anionic or cationic surfactants, preferably selected from the group of hydrocarbon-coupled sulfates, sulfonates or carboxylates or from the group of quarternary ammonium compounds, is used as an ionic surfactant. Particularly preferred, alkyl sulfates or tetraalkyl ammonium salts, especially preferred sodium dodecylsulfate (SDS) and cetyl trimethyl ammonium bromide (CTAS), are employed. These surfactants exhibit a single hydrophilic molecule part (also referred to herein as "surfactant head group") and a single hydrophobic molecule part. The surfactant is preferably used in a concentration of maximally 30 mmol/l, particularly preferred maximally 15 mmol/l.

The surfactant-containing solution is added in portions to the protein-containing solution. Preferably, at least two, particularly preferred at least four, single portions of the surfactant-containing solution are added. The addition in portions has the advantage that the critical micelle formation concentration of the free surfactants is not surpassed in the formed solution so that the micelle formation of the surfactants is prevented extensively and the latter are available for enveloping the protein monomers and oligomers.

The invention has the advantage of providing monomer or oligomer solutions of self-assembling proteins in which the uncontrolled aggregation of the proteins is inhibited. Due to the targeted generation of monomers or oligomers and their stabilization, these coating solutions can be used for position-independent coating of substrate surfaces without their pretreatment.

The protein-containing coating on the substrate can contain within the protein layer one or several different proteins that are capable of self-assemblage. For this purpose, a plurality of molecules of a defined self-assembling protein, preferably of an S-layer protein or hydrophobin or fusion proteins generated therefrom, are used. Alternatively, a mixture of different self-assembling proteins is used, for example, a mixture of a fusion protein, which contains an S-layer protein, with the corresponding S-layer protein. These molecules of the self-assembling proteins are stabilized first in aqueous solution in monomeric or oligomeric form and subsequently are used for coating the substrate.

Upon incubation of the unstabilized protein-containing solution with the surfactant-containing solution that has been added in several portions (in at least two, preferably at least three single portions), the surfactants form with the proteins contained in the aqueous solution a coordinative bond so that a protein-surfactant complex is formed. The uncontrolled formation of protein aggregates is prevented by the formation of the protein-surfactant complex and the protein-containing solution is stabilized. In the meaning of the invention, the stabilization is to be understood therefore as the prevention of an uncontrolled agglomeration of self-assembling proteins in aqueous solutions.

In order to adjust a neutral net charge of the protein oligomers, preferably positively charged metal ions or anions, preferably in the form of an aqueous solution, are added. Protein charges are masked by the formation of protein-ion complexes and the formation of predominant protein oligomers is favored. Particularly preferred are solutions with bivalent metal ions which exhibit a high ion strength, in particular alkaline earth metal ions or metal ions of the transition metal groups I and II of the PTE (periodic table of the elements), which are used in the form of water-soluble salts, preferably in the form of chlorides, nitrates, carbonates, acetates, citrates, gluconates, hydroxides, lactates, sulfates, succinates or tartrates. Particularly preferred are inorganic anions, in particular halides, hydroxides, nitrates, carbonates, sulfates, phosphates but also organic anions, in particular acetates, citrates, succinates or tartrates which have alkali metal ions as counter ions. The concentration of the metal ions or anions in the aqueous solution, as a function of the concentration of the self-assembling proteins, amounts preferably to 0.01 mmol/l to 10 mmol/l, preferably 0.1 mmol/l to 5 mmol/l, and particularly preferred 0.5 mmol/l to 2 mmol/l. Alternatively, the pH value can be shifted by the addition of bases or acids in the direction of the isoelectric point of the employed proteins. When using fusion proteins which contain at least one self-assembling and at least one functional domain, in the subsequent coating step an orientation of the functional domain to the side facing away from the substrate can be advantageously promoted by both treatment steps.

Object of the invention is also an aqueous, protein-containing coating solution which contains monomers or oligomers of self-assembling proteins, wherein the surface-active part of the monomers or oligomers of the self-assembling proteins is enveloped by ionic surfactants.

The invention also encompasses a substrate with a coating of at least one monolayer of self-assembling protein layer, having on the substrate surface at least one monolayer of self-assembling proteins,
and having on the surface of the at least one monolayer of self-assembling proteins a layer which contains at least one ionic surfactant, wherein the surfactant is present in coordinative bond with the self-assembling protein.

In this context, at least one monolayer is assembled directly on the substrate surface. A mediator layer applied by pretreatment, such as e.g. a polylysine or secondary cell wall polymer layer (glycoprotein layer), is not necessary.

Preferably, the self-assembling proteins are recombinant fusion proteins which comprise at least two domains wherein at least one domain is a self-assembling protein domain and one domain is a functional domain or a self-assembling protein domain, wherein the functional domain is arranged on the side of the protein-containing coating facing away from the substrate.

The substrate is preferably a metallic, silicon-containing, ceramic or a polymeric solid.

The invention also encompasses the use of a protein-containing coating solution according to the invention for coating substrate surfaces with at least one monolayer of a self-assembling protein.

For coating a substrate with a monolayer of at least one self-assembling protein, the coating method comprises the steps:
i. providing a stabilized aqueous solution which contains at least one self-assembling protein in that
   a) at least one self-assembling protein is provided in an aqueous solution, and subsequently
   b) in the absence of substances which are suitable for cleaving disulfide bridges, an aqueous solution containing at least one ionic surfactant is added in portions to the protein-containing solution of a), wherein after the addition the final surfactant concentration $c_{surfactant}$ in mol/l is in the following range:

$$\frac{A_{O,protein}}{A_{TKG}} \cdot c_{protein} \cdot 0.516 \leq c_{surfactant} \leq \frac{A_{O,protein}}{A_{TKG}} \cdot c_{protein} \cdot 5.297$$

wherein $A_{O,protein}$ corresponds to the surface of a molecule of the self-assembling protein, $A_{TKG}$ corresponds to the cross-sectional area of the head group of the surfactant, and $c_{protein}$ corresponds to the concentration of the self-assembling protein in mol/l,
ii. contacting the surface of the substrate with the stabilized protein-containing solution whereby a protein-containing coating on the surface of the substrate is generated,
iii. removing the supernatant solution from the coated substrate and/or drying of the coated substrate.

The coating solution as a stabilized aqueous solution according to step a is produced from an aqueous solution of self-assembling proteins in that aggregated protein units are separated in such a way that preferably monomers or oligomers of self-assembling proteins remain in the solution.

For forming and stabilizing monomers of the self-assembling proteins, an aqueous solution containing at least one ionic surfactant is added to the solution, after separation of the protein aggregates, in portions to the protein-containing solution, wherein after addition the final surfactant concentration $c_{surfactant}$ in mol/l is in the following range:

$$\frac{A_{O,protein}}{A_{TKG}} \cdot c_{protein} \cdot 0.516 \leq c_{surfactant} \leq \frac{A_{O,protein}}{A_{TKG}} \cdot c_{protein} \cdot 5.297$$

wherein $A_{O,protein}$ corresponds to the surface of a molecule of the self-assembling protein, $A_{TKG}$ corresponds to the cross-sectional area of the head group of the surfactant, and $c_{protein}$ corresponds to the concentration of the self-assembling protein in mol/l. With such an addition, preferably the surface-active part of each active protein monomer is enveloped by surfactant particles.

With such a coating solution and the coating method, it is possible to generate in a targeted fashion an ordered monolayer of one or several self-assembling proteins on the surface of a substrate in one method step. In this context, in the meaning of the invention an ordered layer or (ordered) monolayer is understood as a protein layer with homogeneous layer thickness (relative standard deviation of the layer thickness preferably maximally 30%). In this context, the average thickness of the layer corresponds to the extension of a molecule of the self-assembling protein.

The coating on the substrate can contain one or several different proteins that are capable of self-assemblage within the protein monolayer. For this purpose, a plurality of molecules of a defined self-assembling protein, preferably of an S-layer protein or hydrophobin or fusion proteins generated therefrom, are used. As an alternative, a mixture of different self-assembling proteins is used, for example, a mixture of a fusion protein, which contains an S-layer protein, with the corresponding S-layer protein. These molecules of the self-assembling proteins are first stabilized in aqueous solution in monomeric form and subsequently used for coating the substrate.

According to the method for coating with a monolayer of self-assembling proteins, a stabilized aqueous solution, which contains the at least one self-assembling protein as a protein monomer, is provided first, wherein the stabilization occurs by addition of at least one surfactant. In this context, the disulfide bridges of the protein structure are not dissolved. The surfactant serves for enveloping protein monomers in a surfactant layer. This occurs in the absence (maximally 0.01 wt. % relative to the self-assembling protein, preferably maximally 0.0001 wt. %) of substances which are suitable for cleaving disulfide bridges (in particular reducing thiols, such as β-mercaptoethanol, dithiothreitol or dithioerythrite). The entire coating method according to the invention is carried out in the absence of these substances.

Upon incubation of the unstabilized protein-containing solution with the surfactant-containing solution added in several portions (in at least two, preferably at least three single portions), the surfactants form with the proteins contained in the aqueous solution a coordinative bond so that a protein-surfactant complex is formed. The uncontrolled formation of multimers of the proteins (aggregates) is inhibited by the formation of the protein-surfactant complex and the protein-containing solution is stabilized. The stabilization is to be understood therefore in the meaning of the invention as prevention of an uncontrolled agglomeration of self-assembling proteins in aqueous solutions. It is possible with the method according to the invention to produce stabilized solutions with protein monomers. The stabilized aqueous solutions available with a method according to the invention are storage-stable and are usable several times for coating of substrates. A stabilized aqueous protein solution available by a method according to the invention is also object of the invention.

Before adding the surfactant, the concentration of the at least one self-assembling protein in the unstabilized aqueous solution after separation of the protein aggregates is preferably at least 5 ng/µl, particularly preferred at least 50 ng/µl, especially preferred at least 90 ng/µl. The unstabilized aqueous solution which contains this at least one self-assembling protein has preferably a pH value of 7 to 9.5. In this context, the solution is preferably a buffered solution.

Optionally, the aqueous solution added in each case is filtered before performing the method according to the invention, preferably by a sterile filter, particularly preferred with a pore size of 0.01 µm-0.5 µm.

In the coating method according to the invention, ionic surfactants (cationic or anionic surfactants) are used for providing the stabilized protein solution. These surfactants have one single hydrophilic molecule part (herein also referred to as "surfactant head group") and at least one hydrophobic molecule part. The surfactant is preferably used in a concentration of maximally 30 mmol/l, particularly preferred maximally 15 mmol/l (method step b). For producing a superficial protein monolayer on the substrate, a surfactant solution (in method step b) is used which contains preferably at least 1 mmol/l, further preferred maximally 15 mmol/l, even more preferred maximally 10 mmol/l, of the surfactant.

The surfactant-containing solution is added in the method step b) in portions to the protein-containing solution. Preferably, at least two, particularly preferred at least four, single portions of the surfactant-containing solution are added. The addition in portions has the advantage that the critical micelle formation concentration of the free surfactants is not surpassed in the formed solution so that the micelle formation of the surfactants is prevented extensively and the latter are available for enveloping the protein monomers.

With the coating method according to the invention, only so much surfactant is added as is necessary to envelope the protein molecules contained in the solution with a bilayer of the surfactant. For this purpose, so much surfactant is added to the solution of a) that the final concentration of the surfactant in mold after the addition to the protein-containing solution is in the following range:

$$\frac{A_{O,protein}}{A_{TKG}} \cdot \frac{N_{Protein}}{N_A} \cdot \frac{\rho_K}{\rho_{up}} \leq c_{surfact.} \leq \frac{A_{O,Protein}}{A_{TKG}} \cdot \frac{N_{Protein}}{N_A} \cdot \frac{\rho_{rc}}{\rho_K} \cdot 2 \quad (1)$$

Herein are: $A_{O,protein}$ ... surface of the self-assembling protein molecule (sphere surface), $A_{TKG}$ ... cross-sectional area of the surfactant head group (surface area of a circle), $N_{protein}$ ... number of monomers of the self-assembling protein per liter, $N_A$ ... Avogadro constant ($N_A=6.022\times10^{23}$ particles/mol), $\rho_{rc}=2.05$, $\rho_K=0.774$, $\rho_{up}=1.5$.

In the relation set forth in equation (1) it is taken into consideration that the surfactant amount which is used for enveloping the protein monomers depends on the available protein surface and hydrophilic or hydrophobic properties of the protein. The radii ratio $\rho_K$ of the protein molecule present as an ideal sphere with the inertia radius $R_G$ relative to the hydrodynamic radius of the protein molecule $R_H$ amounts to 0.774.

One limit range takes into consideration that at least so much surfactant must be added as is required for conversion of a protein present as an ideal sphere to the completely unfolded protein, if exclusively hydrophobic interactions of the surfactant with the protein prevail (left limit range of equation 1). In this case, the radii ratio $\rho_{up}$ of the inertia radius of the unfolded protein molecule $\rho R_G$ relative to the hydrodynamic radius of the protein molecule $R_H$ amounts to 1.5.

The other limit range takes into consideration that at most so much surfactant is added as is required for breaking up protein aggregates existing as "random coil" until the monomeric form of the protein is obtained as an ideal sphere, if exclusively hydrophilic interactions of the surfactant with the protein prevails (right limit range of equation 1). In this case, the radii ratio $\rho_r$ of the inertia radius of the aggregated protein molecule $R_G$ present as random coil relative to the hydrodynamic radius of the protein molecule $R_H$ amounts to 2.05.

With knowledge of the protein concentration in mol/l in the protein-containing solution of a)

$$\frac{N_{protein}}{N_A} = c_{protein} \quad (2)$$

and with the fixed parameters $\rho_{rc}$, $\rho_K$ and $\rho_{up}$ the following correlation results based on equation (1) solely as a function of the self-assembling protein and its surface, the cross-sectional area of the employed surfactant as well as the concentration of the self-assembling protein in the protein-containing solution:

$$\frac{A_{O,protein}}{A_{TKG}} \cdot c_{protein} \cdot 0.516 \leq c_{surfactant} \leq \frac{A_{O,protein}}{A_{TKG}} \cdot c_{protein} \cdot 5.297 \quad (3)$$

In the coating method according to the invention for coating with a monolayer of self-assembling proteins, the surfactant concentration in mol/l that is adjusted in the stabilized protein-containing solution as a coating solution (after addition of the surfactant-containing solution to the protein-containing solution) is in the range indicated in equation (3).

In this context, the surface area of the self-assembling protein molecule arises, when considering a sphere, from the following equation (4), wherein $R_{H,protein}$ is the hydrodynamic radius of the self-assembling protein molecule:

$$A_{O,protein}=4\pi \cdot R_{H,protein}^2 \quad (4)$$

For coating with a monolayer of self-assembling proteins according to an advantageous embodiment of the method, metal ions that are preferably positively charged or anions, preferably in the form of an aqueous solution, are added subsequent to the method step b) to the protein-containing and surfactant-containing solution of method step b). Particularly preferred are bivalent metal ions, in particular alkaline earth metal ions which are used in the form of water-soluble salts, preferably in the form of chlorides, nitrates, carbonates, acetates, citrates, gluconates, hydroxides, lactates, sulfates, succinates or tartrates. Particularly preferred are inorganic anions, in particular halides, hydroxides, nitrates, carbonates, sulfates, phosphates but also organic anions, in particular acetates, citrates, succinates or tartrates which have alkali metals as counter ions. The concentration of the metal ions or anions in the aqueous solution amounts preferably to 0.01 mmol/l to 10 mmol/l, preferably 0.1 mmol/l to 5 mmol/l, and particularly preferred 0.5 mmol/l to 2 mmol/l. When using fusion proteins which contain at least one self-assembling domain and at least one functional domain, in the subsequent coating step an orientation of the functional domain on the side facing away from the substrate can thereby be advantageously promoted.

In the coating method according to the invention, contacting the stabilized protein-containing solution with the surface of the substrate is preferably carried out for at least 15 min, preferably for maximally 48 hours. This method step is carried out preferably at a temperature of 15 to 70° C., particularly preferred above the Krafft point (Krafft temperature) of the used surfactant. During this method step, the self-assembling protein molecules deposit in ordered form in the form of a monolayer on the surface of the substrate. Subsequently, the supernatant protein-containing solution is removed from the substrate in that the solution is preferably either drawn off or the coated substrate is dried (removal of the solvent). When the protein-containing solution is drawn off the substrate, the coated substrate surface is freed by repeated rinsing with deionized water from supernatant, unbonded protein molecules. Drying of the coated substrate occurs preferably by treatment with compressed air.

For coating methods according to the invention, substrates of different structure are suitable. The coating method according to the invention is also suited especially advantageously for porous substrates and enables a homogeneous ordered layer formation also within the pore system that is difficult to access. Preferred substrates are metallic substrates, silicon containing solids (in particular glass or silicon wafers), ceramic or polymeric solids (in particular polytetrafluoroethylene).

With the coating method according to the invention, a substrate is produced which has above the monolayered protein-containing coating a layer which contains the surfactant(s). The surfactant-containing layer present on the surface of the protein-containing coating protects the surface of the protein-containing coating and the self-assembling protein from thermal and chemical stress (and acts thus as a protective coating). The surfactant-containing layer is bonded preferably by coordinative bond to the protein layer.

It is necessary for some applications to remove the surfactant-containing protective coating in order to guarantee the accessibility of the proteins. In a coating method according to the invention, the surfactant-containing layer arranged on the surface of the protein-containing coating located on the substrate is preferably removed for this purpose, wherein for this purpose preferably subsequent to the method step iii):

the coated substrate is washed several times with mechanical action and/or the surfactant layer is removed by buffer treatment by a precipitation reaction.

The used surfactant(s) can be recovered either from the aqueous solution removed in the step iii) from the coated substrate by known methods (for example, by precipitation) and can thereby be reused after a purification step.

A substrate with a protein-containing coating with a monolayer of at least of one self-assembling protein is also encompassed by the invention. The substrate according to the invention has on the substrate surface a monolayer of at least one self-assembling protein and on the surface of the monolayer of the at least one self-assembling protein there is another layer which contains at least one ionic surfactant. In this context, the surfactant with the self-assembling protein is present coordinatively bonded.

Preferably, a substrate according to the invention is available by a coating method according to the invention. On the substrate surface, first the monolayer of the at least one self-assembling protein is thus arranged and another surfactant-containing layer is present thereon.

For coating a substrate with a bilayer of self-assembling proteins, the method with the following steps is carried out:

i. providing a protein-containing coating solution ii. contacting the surface of the substrate with the protein-containing solution, iii. removing the supernatant solution from the coated substrate and/or drying of the coated substrate, wherein for providing the coating solution a) from an aqueous solution of self-assembling proteins aggregated protein units are separated in such a way that monomers or oligomers of self-assembling proteins remain preferably in the solution b) by addition of a solution of ionic surfactants and/or a salt-containing and/or alkaline and/or acidic solution oligomers of the self-assembling proteins are generated and stabilized in the protein-containing coating solution wherein so much ionic surfactant is added that only the surface-active part of each active predominant protein oligomer is enveloped by surfactant particles.

During contacting or before, a solution containing at least one ionic surfactant is added in portions to the protein-containing solution, wherein after the addition the surfactant concentration $C_{surfactant}$ in mol/l is in the following range:

$$\frac{A_{O,Fl}}{A_{O,protein}} \cdot \frac{1}{N_A \cdot V_{Fl}} \leq c_{surfactant} \leq \frac{A_{O,protein\ multimer}}{A_{O,TKG}} \cdot c_{protein} \cdot 0.755$$

wherein $A_{O,Fl}$ corresponds to the total area of the liquid interphase, $A_{O,protein}$ corresponds to the cross-sectional area of the protein (surface area of a circle), $V_{fL}$ corresponds to the total volume of the used liquid, and $N_A$ is the Avogadro constant. $A_{O,protein\ oligomers}$ corresponds to the surface of predominant protein oligomers. $A_{O,TKG}$ corresponds to the cross-sectional area of the surfactant head group (surface area of a circle), and $c_{protein}$ to the used protein concentration.

With the coating method according to the invention, only so much surfactant is added maximally as is necessary to envelope with a bilayer the interphases of the solution with contained protein molecules. For this purpose, so much surfactant is added to the solution from a) that the final concentration of the surfactants in mol/l after the addition to the protein-containing and salt-containing solution is in the following range:

$$\frac{(2 \cdot A_{\square,KF} + x \cdot A_{O,LI})}{A_{O,protein}} \cdot \frac{1}{N_A \cdot V_{Fl}} \leq \quad (5)$$

$$c_{surfactant} \leq \frac{A_{O,protein\ multimer}}{A_{O,TKG}} \cdot \frac{N_{protein}}{N_A} \cdot \frac{\rho_K}{\rho_{rc}} \cdot 2 \quad$$

In this context: $A_{\square,KF}$ ... the contact surface of the liquid with substrate, $A_{O,LI}$ ... the remaining interphase of the liquid, $V_{FL}$ ... the volume of the liquid, $A_{O,protein\ multimer}$ the surface of predominant protein oligomers, $A_{O,TKG}$ ... the cross-sectional area of the surfactant head group (surface area of a circle), $N_{protein}$ ... the number of protein particles in solution ... $N_A$ ... the Avogadro constant ($N_A$=6.022×$10^{23}$ particles/mol), × . . . multiplication factor. $\rho_K$=0.774, $\rho_{rc}$=2.05.

One limit range takes into consideration that maximally so much surfactant is added as is required for the stabilization of predominant protein oligomers. Above a calculable surfactant concentration (right limit range of equation 5), the assembled protein structures (spherical or undefined structure) are decomposed by a direct interaction with surfactant particles with spherical protein particles being separated. The relation presented in equation (5) takes into consideration that the surfactant amount which is used for enveloping the hydrophobin multimers depends on the available multimer surface. The radii ratio $\rho_K$ of the protein particle existing as an ideal sphere of the inertia radius relative to the hydrodynamic radius of the protein molecule $R_H$ is 0.774. The radii ratio $\rho_K$ of the inertia radius $R_G$ of the aggregated hydrophobin multimer present as an undefined structure to the hydrodynamic radius $R_H$ of the protein molecule is 2.05. $A_{O,TKG}$ is determined by scattering experiments with electromagnetic waves or is taken from the literature.

In the second limit range, the generated protein bilayer on the substrate is covered by a deposited surfactant layer and a further deposition of self-assembling proteins at the interphase is inhibited. In order to build an ordered protein bilayer, a defined space on the substrate is available for each protein particle. In order to counteract an unordered growth of the protein layer, contact sites for further protein particles on the substrate coated with a protein bilayer must be blocked by surfactant particles. By the addition of a minimum concentration of surfactants (left limit range of equation 5) a partial surfactant layer is formed on the completely formed protein bilayer and a direct interaction with other assembled protein structures is prevented. The surface $A_{O,protein}$ corresponds to the space requirement of a protein particle on the substrate which must be blocked by at least one surfactant particle to prevent further uncontrolled growth of the protein bilayer. $A_{O,protein}$ can be calculated according to equation 6. In this context: $R_{H,protein}$ . . . hydrodynamic radius of the protein which can be determined by scattering experiments with electromagnetic waves or is to be taken from the literature.

$$A_{O,pro\ TKG}=\pi \cdot R_{H,protein}^{\ 2} \tag{6}$$

With the relation presented in equation (5), it is taken into consideration that the surfactant concentration to be added which is used to prevent further layer growth depends on the total available interphase of the liquid volume that is being used. The contact surface of the liquid with the substrate ($A_{\square,KF}$) and the remaining adjoining interphases ($A_{O,\ LI}$) is calculated in this context from their geometrical parameters.

Taking into account that the preferred orientation of the surfactant particles at interphases depends of their wettability (hydrophilic or hydrophobic), a corrective term x which can be preferably of the values 1 and 2 is inserted in equation (5). At hydrophilic-hydrophilic interfaces, the surfactant particles deposit preferably as a bilayer on the substrate (x=2). In contrast to this, preferably the formation of a surfactant monolayer (x=1) dominates at hydrophilic-hydrophobic interfaces.

Contacting the stabilized protein-containing coating solution with the surface of the substrate in the coating method according to the invention is done preferably for at least 15 min, preferably for maximally 48 hours. This method step is carried out preferably at a temperature of 15 to 70° C., particularly preferably above the Krafft point (Krafft temperature) of the used surfactant. During this method step, the protein oligomers deposit in ordered form in the form of a protein bilayer on the surface of the substrate. Subsequently, the supernatant protein-containing solution is removed from the substrate in that the solution is preferably drawn off. Subsequently, the coated substrate surface is freed of supernatant non-bonded protein molecules by repeated rinsing with deionized water. As an alternative to storage in aqueous solutions, drying of the coated substrate (removal of the solvent) can occur; preferably by treatment with compressed air.

For coating a substrate with a hydrophobin-bilayer of at least one hydrophobin type, the method is carried out advantageously with the following steps:

i. providing a stabilized aqueous solution which contains hydrophobins of at least one hydrophobin type in that
   a) the hydrophobins are provided in an aqueous solution, and
   b) as a function of the charge of the hydrophobins, a salt-containing and/or alkaline or acidic solution, for masking the hydrophobin charges or for adjusting a neutral net charge of the hydrophobins, is added in portions and for a period of 1 to 60 min for formation of predominant hydrophobin multimers,
ii. contacting the surface of the substrate with the stabilized hydrophobin-containing solution by which a protein-containing coating on the substrate is generated, wherein either during contacting or before a solution containing at least one ionic surfactant is added in portions to the protein-containing solution, wherein after the addition the surfactant concentration $c_{surfactant}$ in mol/l is in the following range:

$$\frac{A_{O,Fl}}{A_{O,protein}} \cdot \frac{1}{N_A \cdot V_{Fl}} \leq c_{surfactant} \leq \frac{A_{O,protein\ multimer}}{A_{O,TKG}} \cdot c_{protein} \cdot 0.755$$

wherein $A_{O,Fl}$ is the total area of the liquid interphase, $A_{O,protein}$ is the cross-sectional area of the protein (surface area of a circle), $V_{fL}$ is the total volume of the used liquid, and $N_A$ is the Avogadro constant. $A_{O,protein\ multimer}$ corresponds to the surface of predominant hydrophobin multimers, $A_{O,TKG}$ corresponds to the cross-sectional area of the surfactant head group (surface area of a circle), and $c_{protein}$ to the used hydrophobin concentration.
iii. removing the supernatant solution from the coated substrate and/or drying the coated substrate.

Predominant multimers refer to oligomers with maximally 10 protein units.

With this coating process, it is possible to generate in a targeted fashion an ordered bilayer of one or several "fusion hydrophobins" on the surface of a substrate in one method step. In this context, in the meaning of the invention an ordered layer or (ordered) bilayer is to be understood as a hydrophobin layer with homogeneous layer thickness (relative standard deviation of the layer thickness preferably maximally 30%). In this context, the average thickness of the layer corresponds to the extension of two molecules of the hydrophobin.

In order to be able to guarantee the build-up of a homogeneous hydrophobin layer, two opposing protein properties must be balanced. The assemblage of hydrophobin monomers is based on the interaction of two different physical values. On the one hand, the assemblage of identical hydrophobin monomers strongly depends on the accessibility of two separated hydrophobin regions which differ with respect to their polarizability (hydrophilicity or hydrophobicity). In this context, the interaction of two identically polarizable regions of hydrophobin particles leads in this context to attraction between the hydrophobin particles, those of oppositely polarizable regions leads to repulsion. On the other hand, the electric net charge of the hydrophobins must be considered. In order to prevent a repulsion of hydrophobin particles of same charge, the used hydrophobins must have a neutral net charge. The method according to the invention allows a targeted intervention in these interactions and enables coating of a substrate with a defined hydrophobin bilayer.

According to the method according to the invention, a stabilized aqueous solution which contains at least one hydrophobin type is provided first, wherein the stabilization is realized through addition of at least a salt, a base or an acid. The formation of predominant hydrophobin multimers with compensation of protein charges is promoted by the addition of salts, bases or acids.

The coating on the substrate can contain one or several different hydrophobin types within the hydrophobin bilayer. A plurality of molecules of a defined hydrophobin or of fusion proteins produced therefrom are used for this purpose. As an alternative to this, a mixture of different self-assembling hydrophobins, for example, a mixture of a fusion protein which contains at least one hydrophobin, is used. These molecules of the hydrophobins are stabilized first in aqueous solution, subsequently an ordered formation of predominant assembled structures is induced and finally used for coating the substrate.

Upon incubation of the hydrophobin-containing solution with the salt-containing solution added in several portions (in at least two, preferably at least three, single portions), the counter ions form a coordinative bond with the hydrophobins contained in the aqueous solution so that a hydrophobin-counter ion complex is formed. The controlled formation of multimers of the hydrophobins (assembled structures) is triggered by the formation of the hydrophobin-counter ion complex and the protein-containing solution is stabilized. The stabilization in the meaning of the invention is thus to be understood as the prevention of an uncontrolled agglomeration of hydrophobins in aqueous solutions. It is possible with the method according to the invention to produce stabilized solutions with hydrophobin multimers (preferably dimers or tetramers). The stabilized aqueous solutions available by a method according to the invention are usable for coating substrates.

Before addition of the salt, the base or acid, the concentration of the at least one hydrophobin type in the unstabilized aqueous solution is preferably at least 50 ng/µl, particularly preferred at least 90 ng/µl. The unstabilized aqueous solution which contains at least one self-assembling hydrophobin type shows preferably a pH value of 7 to 9.5. In this context, the solution is preferably a buffered solution.

In the coating method according to the invention, for providing the stabilized protein solution preferably positively charged metal ions or anions are added, preferably in the form of an aqueous solution, in order to adjust a neutral net charge of the hydrophobins. Hydrophobin charges are masked by the formation of hydrophobin-ion complexes and the formation of predominant hydrophobin multimers is favored. Particularly preferred are solutions with bivalent metal ions which exhibit a high ion strength, in particular alkaline earth metal ions which are used in the form of water-soluble salts, preferably in the form of chlorides, nitrates, carbonates, acetates, citrates, gluconates, hydroxides, lactates, sulfates, succinates or tartrates. Particularly preferred are inorganic anions, in particular halides, hydroxides, nitrates, carbonate, sulfates, phosphates but also organic anions, in particular acetates, citrates, succinates or tartrates which have alkali metals as counter ions. The concentration of the metal ions or anions in the aqueous solution is preferably 0.01 mmol/l to 10 mmol/l, preferably 0.1 mmol/l to 5 mmol/l, and particularly preferred 0.5 mmol/l to 2 mmol/l. Alternatively, the pH value can be shifted by the addition of bases or acids in the direction of the isoelectric point of the employed hydrophobins. When using fusion proteins which contain at least one self-assembling domain and at least one functional domain, an orientation of the functional domain to the side facing way from the substrate can be advantageously promoted in the next coating step with both treatment steps.

The addition is carried out in portions, preferably with identical portions, and preferably in at least two parts, particularly preferred in 3 portions, and for a period of time of 1 to 60 min in order to inhibit an uncontrolled hydrophobin aggregation.

During contacting of the substrate or before, solutions of ionic surfactants, preferably cationic and/or anionic surfactants, are added to the protein-containing and salt-containing solution. These surfactants have a hydrophilic molecule part (herein also referred to as "surfactant head group") and a hydrophobic molecule part. For producing a protein bilayer on the substrate, a surfactant concentration which corresponds preferably to at least 1 µmol/l and maximally 500 µmol/l, particularly preferably maximally 100 µmol/l, is adjusted by addition of a surfactant-containing solution.

With the coating method according to the invention, only so much surfactant is added maximally as is necessary to envelope with a bilayer the interphases of the solution with the protein molecules contained therein. For this purpose, so much surfactant is added to the solution of b) that the final concentration of the surfactant in mol/l after the addition to the protein-containing and salt-containing solution is in the following range:

$$\frac{(2 \cdot A_{\square,KF} + x \cdot A_{O,LI})}{A_{O,protein}} \cdot \frac{1}{N_A \cdot V_{Fl}} \leq \qquad (5)$$

$$c_{surfactant} \leq \frac{A_{O,protein\ multimer}}{A_{O,TKG}} \cdot \frac{N_{protein}}{N_A} \cdot \frac{\rho_K}{\rho_{rc}} \cdot 2$$

In this context: $A_{\square,KF}$ . . . contact surface of the liquid with substrate, $A_{O,LI}$ . . . remaining interphase of the liquid, $V_{FL}$ . . . volume of the liquid, $A_{O,protein\ multimer}$ the surface of predominant hydrophobin multimers, $A_{O,\ TKG}$ . . . cross-sectional area of the surfactant head group (surface area of a circle), $N_{protein}$ . . . number of protein particles in solution, $N_A$ . . . Avogadro constant ($N_A$=6.022×10$^{23}$ particles/mol), x . . . multiplication factor. $\rho_K$=0.774, $\rho_{rc}$=2.05.

One limit range takes into consideration that maximally so much surfactant is added as is necessary for breaking up predominant hydrophobin multimers. Above a calculable surfactant concentration (right limit range of equation 5), assembled hydrophobin structures (spherical or undefined structure) are decomposed by a direct interaction with surfactant particles with separation of spherical hydrophobin particles. With the relation provided in equation (5), it is taken into consideration that the surfactant amount which is used for enveloping the hydrophobin multimers depends on the available multimer surface. The radii ratio $\rho_K$ of the hydrophobin particle existing as an ideal sphere with the inertia radius $R_G$ relative to the hydrodynamic radius of the protein molecule $R_H$ amounts to 0.774. The radii ratio $\rho_{rc}$ of the inertia radius of the aggregated hydrophobin multimers $R_G$ that is present as an undefined structure relative to the hydrodynamic radius of the protein molecule $R_H$ amounts to 2.05. $A_{O,TKG}$ is determined by scattering experiments with electromagnetic waves or is taken from the literature.

In the second limit range case, the formed protein bilayer on the substrate is covered by a deposited surfactant layer and a further deposition of hydrophobins at the interphase is prevented. In order to build up an ordered hydrophobin bilayer, a defined space on the substrate is available for each hydrophobin particle. In order to counteract an unordered growth of the hydrophobin layer, contact sites for other hydrophobin particles on the substrate that is coated by a hydrophobin bilayer must be blocked by surfactant particles. By the addition of a minimum concentration of surfactant (left limit range of equation 5) a partial surfactant layer is formed on the completely formed hydrophobin bilayer and a direct interaction with other assembled hydrophobin structures is inhibited. The surface $A_{O,protein}$ corresponds to the space requirement of a hydrophobin particle on the substrate which must be blocked by at least one surfactant particle in order to prevent further uncontrolled growth of the hydrophobin bilayer. $A_{O,protein}$ can be calculated based on equation 6. In this context, $R_{H,protein}$ ... is the hydrodynamic radius of the hydrophobin which can be determined by scattering experiments with electromagnetic waves or is to be taken from the literature.

$$A_{O,pro\ TKG} = \pi \cdot R_{H,protein}^2 \quad (6)$$

With the relation provided in equation (5), it is taken into consideration that the surfactant concentration to be added which is used for prevention of further layer growth depends on the total available interphase of the liquid volume that is being used. The contact surface of the liquid with the substrate ($A_{\square,KF}$) and the remaining adjoining interphases ($A_{O,LI}$) is calculated in this context based on their geometrical parameters.

Taking into account that the preferred orientation of the surfactant particles at interphases depends on their wettability (hydrophilic or hydrophobic), a corrective term x which may assume preferably the values 1 and 2 is inserted in equation (5). At hydrophilic-hydrophilic interfaces surfactant particles deposit preferably as a bilayer on the substrate (x=2). In contrast to this, preferably the formation of a surfactant monolayer (x=1) dominates at hydrophilic-hydrophobic interfaces.

Contacting of the stabilized hydrophobin-containing solution with the surface of the substrate in the coating method according to the invention is carried out preferably for at least 15 min, preferably for maximally 48 hours. This method step is carried out preferably at a temperature of 15 to 70° C., particularly preferably above the Krafft point (Krafft temperature) of the used surfactant. During this method step, the assembled hydrophobin structures deposit in ordered form in the form of a protein bilayer on the surface of the substrate. Subsequently, the supernatant protein-containing solution is removed from the substrate in that the solution is preferably drawn off. Subsequently, the coated substrate surface is freed from supernatant non-bonded protein molecules by repeated rinsing with deionized water. As an alternative to the storage in aqueous solutions, drying of the coated substrate (removal of the solvent) can be carried out; preferably by treatment with compressed air.

For the coating method according to the invention, substrates of different structure are suitable. The coating method according to the invention is especially advantageously suited also for porous substrates and allows a homogeneous ordered layer construction also within the pore system that is difficult to access. Preferred substrates are metallic substrates, silicon-containing solids (in particular glass or silicon wafers), ceramic or polymeric solids (in particular polytetrafluoroethylene).

By the coating method according to the invention, a substrate is produced which has above the bilayered protein-containing coating a layer which contains the surfactant(s). The surfactant-containing layer that is present on the surface of the protein-containing coating protects the surface of the protein-containing coating and the hydrophobin from thermal and chemical stress (and acts thus as a protective coating). The surfactant-containing layer is bonded preferably by coordinative bond to the protein layer.

It is necessary for some applications to remove the surfactant-containing protective coating in order to guarantee the accessibility of the proteins. In a coating method according to the invention the surfactant-containing layer arranged on the surface of the hydrophobin containing coating located on the substrate is preferably removed for this purpose, wherein for this purpose preferably subsequent to the method step ii):

the coated substrate is washed several times with mechanical action and/or the surfactant layer is removed by buffer treatment by a precipitation reaction.

The used surfactant(s) can either be recovered from the aqueous solution drawn off in the step iii) from the coated substrate by known methods (for example, by precipitation) and can thereby be reused after a purification step.

As a hydrophobin, hydrophobins of the class I, preferably Ccg2 from *Neurospora crassa*, or hydrophobins of the class II, preferably HFBI or HFBII from *Trichoderma reesei*, are used.

The invention is especially advantageously suitable for functionalized hydrophobins because the accessibility of the functionalization can be guaranteed due to the ordered layer configuration of bilayers of the functionalized hydrophobin. It is advantageously possible to carry out the coating of the substrate in such a way that the functionalization is present at the side of the protein-containing coating facing away from the substrate.

Preferably, as a hydrophobin a recombinant fusion protein is used which comprises at least two domains, wherein one domain is a self-assembling protein domain and one domain a functional domain or self-assembling protein domain.

Hence, the hydrophobin is preferably a recombinant fusion protein, i.e., a protein which is produced by genetically modified organisms. By fusion of the genes of two or more protein domains that do not exist in this combination in nature and that are usually connected with each other by flexible linker structures (linker peptides), the recombinant fusion protein is obtainable by expression of the fused genes. For the heterologous gene expression the artificially generated reading frame of the DNA construct is flanked in 5' position by a host-specific promoter and in 3' position by a terminator. A recombinant fusion protein used in the invention comprises at least two domains, wherein one domain is a self-assembling protein domain (preferably selected from the aforementioned hydrophobins) and one domain is a functional domain. Preferred functional domains are fluorescent protein domains, catalytic domains or protein domains with enzyme activity. For generating a dimeric hydrophobin, other hydrophobins can also act as a fusion domain. The choice of suitable fusion partner parts is not limited in this regard to proteins of certain organisms. For a selective isolation of the fusion proteins from the cell lysate, the amino acid sequence can have additionally an affinity domain with 1-20 amino acids in the N-terminal and/or C-terminal region. They can interact as a specific anchoring group with complementary groups on solid supports.

The aqueous solution containing at least one hydrophobin type to which the salt-containing, basic and/or acidic as well as surfactant-containing solutions are added, contains in one embodiment variant mixtures of different hydrophobin types, preferably at least one functionalized hydrophobin type in combination with at least one non-functionalized hydrophobin type. The stability of the protein-containing coating is thereby improved. This embodiment variant is advantageous particularly for functionalized hydrophobins with large functional domains in order to enable the interaction between assembling domains of different protein molecules.

In a coated substrate according to the invention which contains recombinant fusion protein as a hydrophobin, the functional domain of the recombinant fusion protein is arranged preferably on the side of the protein-containing coating facing away from the substrate. The hydrophobin domain of the recombinant fusion protein is arranged on the side of the protein-containing coating that is facing the substrate. The coating that contains at least one surfactant is arranged therefore in this case above the functional domain of the recombinant fusion protein.

As a surfactant, an anionic or cationic surfactant is used, preferably selected from sodium dodecylsulfate (SDS) and cetyl trimethyl ammonium bromide (CTAB).

A method for stabilizing monomers of at least one self-assembling protein in an aqueous solution is also encompassed by the invention (herein also referred to as "stabilization method"). In the stabilization method according to the invention
a) an aqueous solution, preferably of an aqueous buffer solution, is added to at least one self-assembling protein, and subsequently
b) in the absence of substances which are suitable for cleaving disulfide bridges, an aqueous solution containing at least one ionic surfactant is added in portions to the protein-containing solution of a), wherein after the addition the final surfactant concentration $c_{surfactant}$ in mol/l is in the following range;

$$\frac{A_{O,protein}}{A_{TKG}} \cdot c_{protein} \cdot 0.516 \leq c_{surfactant} \leq \frac{A_{O,protein}}{A_{TKG}} \cdot c_{protein} \cdot 5.297,$$

wherein $A_{O,protein}$ corresponds to the surface of a molecule of the self-assembling protein, $A_{TKG}$ corresponds to the cross-sectional area of the head group of the surfactant, and $c_{protein}$ to the concentration of the self-assembling protein in mol/l.

Other embodiments of the stabilization method according to the invention are analog to the embodiments of the coating method according to the invention.

A stabilized aqueous protein-containing solution, preferably obtainable by a method according to the invention, which contains at least one self-assembling protein and at least one surfactant is also subject matter of the invention (the terms "stabilized aqueous solution" and "stabilized monomers in aqueous solution" are synonymously used herein). Stabilized protein monomer solutions are preferred.

The stabilized aqueous solution according to the invention contains at least one self-assembling protein, at least one ionic surfactant, and contains no substances which are suitable for cleaving disulfide bridges (maximally 0.01 wt. % relative to the self-assembling protein, preferably maximally 0.0001 wt. %). In the aqueous solution according to the invention, monomers of the self-assembling protein are present in coordinative bond with the ionic surfactant (protein-surfactant complex). The surfactant concentration $c_{surfactant}$ in mol/l in the aqueous solution is in the following range:

$$\frac{A_{O,protein}}{A_{TKG}} \cdot c_{protein} \cdot 0.516 \leq c_{surfactant} \leq \frac{A_{O,protein}}{A_{TKG}} \cdot c_{protein} \cdot 5.297$$

In this context, $A_{O,protein}$ corresponds to the surface of a molecule of the self-assembling protein, $A_{TKG}$ to the cross-sectional area of the head group of the surfactant, and $c_{protein}$ to the concentration of the self-assembling protein in mol/l.

The invention also encompasses a substrate with a coating of a hydrophobin bilayer on whose substrate surface a bilayer of at least one hydrophobin type is located, wherein on the surface of the hydrophobin bilayer a layer is arranged which contains at least one ionic surfactant, wherein the surfactant is present in coordinative bond with the hydrophobin of the surface of the bilayer. In this context, the hydrophobins of the at least one hydrophobin type are preferably recombinant fusion proteins which encompass at least two domains, wherein one domain is a self-assembling protein domain and one domain is a functional domain or a self-assembling protein domain, wherein the functional domain is arranged on the side of the hydrophobin containing coating that is facing away from the substrate.

The substrate is preferably a metallic, silicon-containing, ceramic or a polymeric solid.

The invention also encompasses the use of a stabilized protein-containing solution according to the invention for coating substrate surfaces with a monolayer of a self-assembling protein.

The following embodiments are preferred for the invention:

The self-assembling protein is selected preferably from hydrophobins and surface layer proteins (S-layer proteins). Preferred hydrophobins are hydrophobins of the class I, preferably Ccg2 from *Neurospora crassa*, or hydrophobins of the class II, preferably HFBI or HFBII from *Trichoderma reesei*. Preferred S-layer proteins are SbsC from *Bacillus stearothermophilus*, S13240 from *Bacillus stearothermophilus* or SsIA from *Sporosarcina ureae*.

The invention is especially advantageously suitable for functionalized self-assembling proteins because the accessibility of the functionalization can be guaranteed by the ordered layer construction of monolayers of the functionalized self-assembling protein. It is advantageously possible to carry out coating of the substrate in such a way that the functionalization is present on the side of the protein-containing coating facing away from the substrate.

Preferably, the self-assembling protein is therefore a recombinant fusion protein, i.e., a protein which is produced by genetically modified organisms. By fusion of the genes of two or more protein domains that do not exist in this combination in nature and are usually connected with each other by flexible linker structures (linker peptides), the recombinant fusion protein is obtainable by expression of the fused genes. A recombinant fusion protein used in the invention encompasses at least two domains, wherein one domain is a self-assembling protein domain (preferably selected from the aforementioned self-assembling proteins) and one domain is a functional domain. Preferred functional domains are fluorescent protein domains, catalytic domains or protein domains with enzyme activity.

The aqueous solution containing at least one self-assembling protein to which the surfactant-containing solution is added contains in one embodiment variant mixtures of self-assembling proteins, preferably at least one functionalized self-assembling protein in combination with at least one non-functionalized self-assembling protein. The stability of the protein-containing coating is thereby improved. This embodiment variant is advantageous particularly for functionalized self-assembling proteins with large functional domains in order to enable the interaction between assembling domains of different protein molecules.

In a coated substrate according to the invention which contains recombinant fusion protein as a self-assembling protein, the functional domain of the recombinant fusion protein is preferably arranged on the side of the protein-containing coating facing away from the substrate. The self-assembling protein domain of the recombinant fusion protein is arranged on the side of the protein-containing coating that is facing the substrate. The coating which contains at least one surfactant is arranged therefore in this case above the functional domain of the recombinant fusion protein.

The surfactant is an anionic or cationic surfactant, preferably selected from sodium dodecylsulfate (SDS) and cetyl trimethyl ammonium bromide (CTAB).

The invention offers the advantage of providing stabilized monomer solutions of self-assembling proteins in which the uncontrolled aggregation of the proteins is inhibited. By means of targeted monomerization and stabilization of the solution, the latter can be used for position-independent coating of substrate surfaces.

BRIEF DESCRIPTION OF THE DRAWINGS

With the aid of the following figures and examples, the invention will be explained in more detail without limiting the invention thereto.

DESCRIPTION OF PREFERRED EMBODIMENTS

Figure 1:
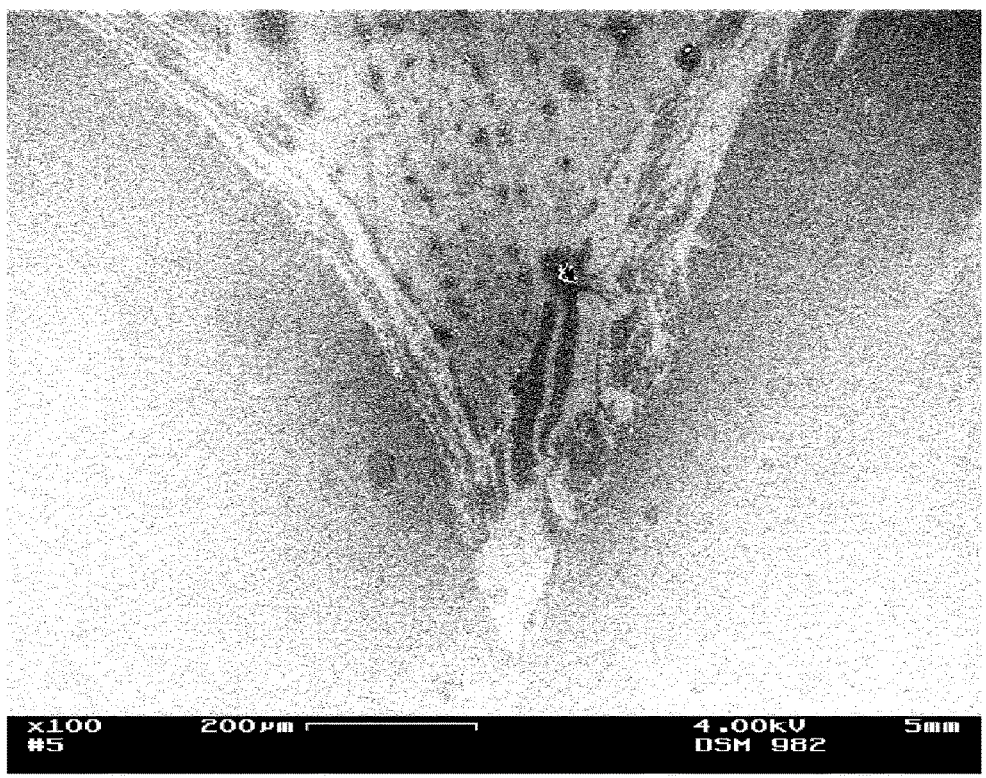
FIG. 1 SEM image of a silicon wafer coated with a monolayer of the S-layer protein SbsC-(R5P)$_2$ from *Bacillus stearothermophilus* with deposited SDS layer. The homogeneous areas to the left and the right show the protein monolayer from which the SDS layer (shown in the middle) has been removed.

Example 1: Expression of Recombinant Self-Assembling Fusion Proteins in *E. coli* and Purification The recombinant fusion proteins listed in Table 1 were generated which each have at the N terminal the self-assembling protein domain and at the C terminal a functional domain listed therein.

TABLE 1

| fusion protein | self-assembling domain | functional domain |
|---|---|---|
| HFBI-(R5P)$_2$ | class II hydrophobin HFBI (*Trichoderma reesei*) | subunit of silaffin (*Cylindrotheca fusiformis*) |
| HFBI-(XSR5P)$_3$ | class II hydrophobin HFBI (*Trichoderma reesei*) | shortened subunit of silaffin (*Cylindrotheca fusiformis*) |
| Ccg2-HA | class I hydrophobin Ccg2 (*Neurospora crassa*) | human influenza hemaglutinin tag |
| S13240-HA | S-layer protein S13240 (*Geobacillus stearothermophilus*) | human influenza hemaglutinin tag |
| SbsC-HA | S-layer protein SbsC (*Geobacillus stearothermophilus*) | human influenza hemaglutinin tag |
| SbsC-(R5P)$_2$ | S-layer protein SbsC (*Geobacillus stearothermophilus*) | subunit of silaffin (*Cylindrotheca fusiformis*) |
| SbsC-(XSR5P)$_3$ | S-layer protein SbsC (*Geobacillus stearothermophilus*) | shortened subunit of silaffin (*Cylindrotheca fusiformis*) |
| SslA | S-layer protein SslA (*Sporosacina ureae*) | no functional domain |

The DNA sequences coding for the respective domain are amplified by means of polymerase chain reaction (PCR) for this purpose and, by means of overlap PCR, a fusion gene was fused. The used flanking primers contained recognition sequences for the restriction endonucleases NdeI and XhoI. After vector and fragment restriction by means of the corresponding endonucleases, ligation, and transformation in *Escherichia coli* (*E. coli*) as a host organism, the presence of the fusion gene in the generated plasmids was checked.

For the production of the fusion protein containing the self-assembling protein, the plasmids which contained the generated fusion gene correctly, were transformed in the *E. coli* strain SHuffle® T7 Express. The fusion protein is concentrated in the bacterial cells intracellularly.

The transformed *E. coli* cells were cultured at 30° C. The expression of the fusion gene was induced by addition of 0.4 mM (mmol/l) IPTG. After 4-6 h, the cells were pelleted by means of centrifugation (at 4,000×g, 4° C., 10 min). After washing the cell pellet 2 times with 50 mM tris buffer (pH 7.5), the cells once more were pelleted by centrifugation. For cell disruption, the *E. coli* cells were subjected thrice to an ultrasonic treatment (9 cyc., 70%, 4° C., 2 min) and three times to a subsequent French Press treatment (20,000 psi). The disrupted bacterial cells were washed twice with 50 mM tris buffer (pH 7.5). For protein extraction the disrupted cells were taken up in 1 ml lysis buffer and incubated at 23° C. for 30 min. The purification of the fusion protein was carried out by means of nickel affinity chromatography. The elution of the fusion protein occurred in an isotype composed phosphate buffer (pH 4.5) with 250 mM imidazole.

In order to transfer the protein into an active state, the obtained eluate was dialyzed against the 4.000-fold volume of a dialysis buffer at 4° C. for maximally 48 h. For the dialysis of hydrophobins a tris buffer (50 mM, pH 8.5 reduced with 1 mM glutathione and oxidized with 0.2 mM glutathione) was used. For the dialysis of surface layer proteins, 10 mM of tris buffer (pH 9.0) was used as a dialysis buffer.

Example 2: Production of a Protein Monolayer on a Silicon Wafer

An ordered protein monolayer of a self-assembling protein, as obtained in Example 1, was generated on a silicon wafer. For this purpose, the fusion protein HFBI-(XSR5P)$_3$ was employed which contains a class I hydrophobin (HFBI from *Trichoderma reesei*) as a self-assembling domain and contains as a functional domain a human influenza hemaglutinin tag.

First, for sedimentation of larger protein aggregates, a centrifugation (15 min at 18,000×g, 4° C.) was carried out and the protein concentration determined (according to Lowry). The sediment was taken up in 50 mM tris buffer pH 8.5. A protein concentration of 100 ng/µl was adjusted.

To this protein-containing solution a filtered 8 mM sodium dodecylsulfate (SDS) was added in four single portions for a period of time of 10 min. For HFBI-(XSR5P)$_3$ the added surfactant quantity per liter of a solution adjusted to a protein concentration of 100 ng/µl was 2 mmol so that a final surfactant concentration of 2 mmol/l was adjusted in the solution.

Based on equation (3), for a 100 ng/µl protein solution the surfactant concentration is to be adjusted to between 0.5 mmol/l and 5.6 mmol/l. The self-assembling fusion protein HFBI-(XSR5P)$_3$ has a molecular weight of about 14,000 g/mol. For a protein concentration in the solution of 100 ng/µl, the concentration in mol/l accordingly amounts to $7.14*10^{-6}$ mol/l. The surfactant head group of the used SDS molecule has an effective surface area of $A_{TKG}$ of 0.62 nm$^2$. The protein molecule has a hydrodynamic radius $R_N$ of 2.7 nm. Based on this, a protein surface area of $A_{O,protein}$=91.6 nm$^2$ results from equation (4).

The stabilized solution obtained in this manner was clear and was stable for at least five days when stored at 20° C.

The stabilized solution which contains monomers of the self-assembling protein was used for coating a silicon wafer with edge lengths 1×1 cm. For this purpose, 100 µl of the stabilized protein-containing solution was applied onto a silicon wafer with incubation for at least 30 min. Subsequently, the supernatant solution was drawn off and the silicon wafer coated with HFBI-(XSR5P)$_3$ washed in filtered, twice distilled water. The storage of the coated silicon wafer was done in the dialysis buffer mentioned in Example 1.

Subsequently, the drawn-off stabilized protein solution was employed in other coating processes.

In order to make accessible the functional domain of the self-assembling fusion protein on the substrate, remaining surfactant was removed from the coated substrate by means of precipitation reaction.

Example 3: Characterization of the Coating with HFBI-(XSR5P)$_3$ on a Silicon Wafer Prepared in Example 2 by Means of Ellipsometry The coated silicon wafer obtained in Example 2 was examined by ellipsometry (Multiskop of the company OPTREL (Berlin)). The change of the polarization plane of a monochromatic laser beam (wavelength 632.8 nm) was determined by reflection at an angle of 136°. By measuring the intensity of the perpendicular ($R_S$) and parallel ($R_p$) reflected planes of incidence of the polarized light beam, the intensity ratio ($\rho$) was determined. The ellipsometric angles $\Delta$ and $\Psi$ are derived from the FRENSEL equations. By including in the calculation the refractive indices of the single layers, the layer thickness of the uppermost layer was calculated.

$$\rho = \frac{R_p}{R_s} = \frac{|R_p|}{|R_s|} e^{i(\delta_p - \delta_s)} = \tan(\Psi)e^{i\Delta}$$

In this context, $\delta_p$ and $\delta_s$ indicate the phase difference to the zero point of light polarized perpendicular and in parallel. The optical constants known from the literature were used for silicon as a substrate and silicon dioxide. As refractive index of the protein film 1.375 was used.

The determined layer thickness of HFBI-(XSR5P)$_3$ on the silicon wafer amounted to 13.2±0.2 Å. This corresponds to the literature values of a monolayer of the self-assembling protein.

The following Table 2 shows the ellipsometric data of an analysis of four different specimens (1 to 4, the different values in the individual row were taken at different measuring points on the respective specimen):

TABLE 2

|  | 1 | 2 | 3 | 4 | | |
|---|---|---|---|---|---|---|
| $\square_{SiO2}$ [°] | 175.87 | 175.772 | 175.761 | 175.879 | | |
| $d_{SiO2}$ [Å] | 16.5 | 17.0 | 17.0 | 16.5 | | |
| | 173.216 | 173.172 | 173.138 | 173.168 | | |
| | 173.26 | 173.297 | 173.138 | 173.509 | | |
| | 173.324 | 173.09 | 173.362 | 173.166 | | |
| | 173.334 | 173.211 | | 173.45 | | |
| | 173.37 | 173.096 | | 173.436 | | |
| | | 173.06 | | | | |
| $\square_{protein}$ [°] | 173.301 | 173.154 | 173.213 | 173.346 | | |
| | | | | | | standard |
| | 0.062 | 0.090 | 0.129 | 0.166 | average | deviation |
| $D_{protein}$ [Å] | 13.2 | 13.4 | 13.1 | 13 | 13.2 | 0.2 |

Example 4: Scanning Electron Microscopy (SEM) of a Silicon Wafer Coated with SbsC-(R5P)$_2$ A silicon wafer was coated analog to Example 2 with the self-assembling protein SbsC-(R5P)$_2$ (Table 1). The obtained coated silicon wafer was examined by means of SEM (Zeiss DSM 982 Gemini). For the analysis, the coated silicon wafer was dried and subsequently metallized with an atomic gold layer. The results of the SEM analysis are shown in FIG. 1. Bright areas indicated therein the protein layer with a deposited SDS layer. The dark areas indicate the protein as a monolayer from which the SDS layer has been removed.

Example 5: Atomic Force Microscopy (AFM) of a Silicon Wafer Coated with Ccg2-HA

Figure 2:
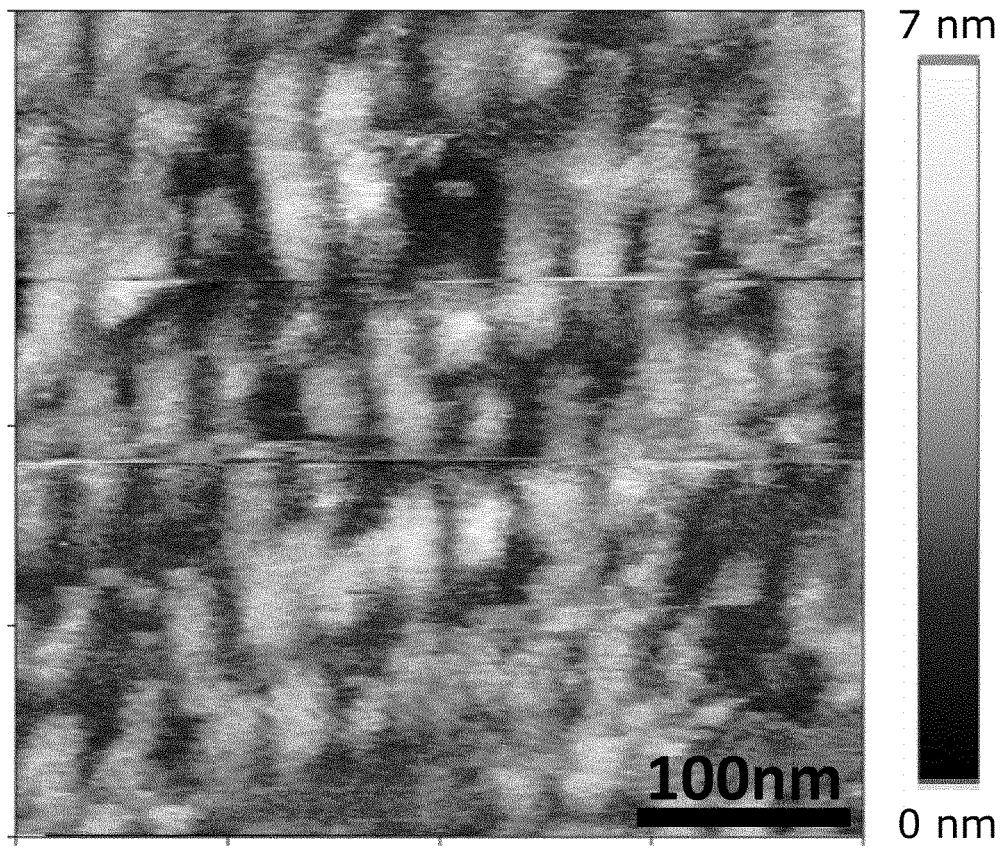
FIG. 2 AFM image of a silicon wafer coated with a monolayer of the class 1 hydrophobin Ccg-2 from *Aspergillus nidulans* after removal of the SDS layer with exposed protein monolayer.
Figure 3:
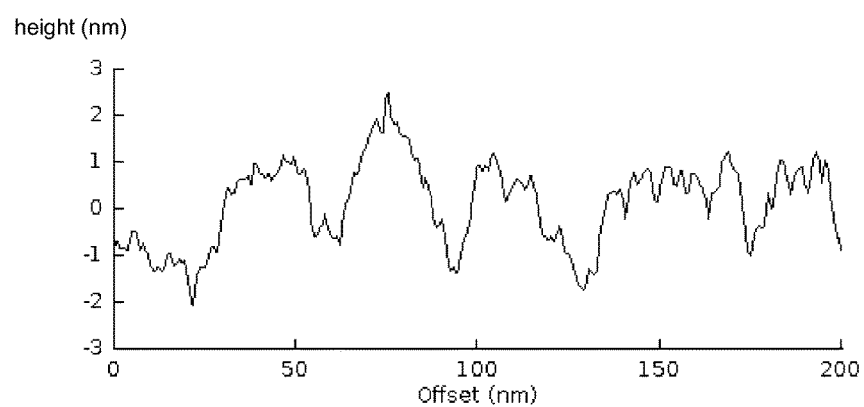
FIG. 3 height profile of a silicon wafer coated with a monolayer of the class 1 hydrophobin Ccg-2 from *Aspergillus nidulans* determined by AFM.

A silicon wafer coated analog to Example 2 with Ccg2-HA was examined in an aqueous environment by means of AFM. The results of the AFM analysis are shown in FIG. 2. A uniform protein monolayer can be seen. The Ccg2 tube structures have a length of about 100 nm (FIG. 2, bright areas). The height profile (FIG. 3) shows that the self-assembled structures of Ccg2-HA have a width of about 25 nm and a height of about 2.5 nm.

Example 6: Exposing Functional Domains for Self-Assembling Fusion Proteins

With the self-assembling fusion protein HFBI-(R5P)$_2$ produced in Example 1, a silicon wafer was coated with a monolayer of the protein analog to Example 2. The layer thickness, which was determined ellipsometrically analog to Example 3, amounted to 13.8±0.4 Å. In the fusion protein the functional domain, the R5P subunit of silaffin, is fused with the hydrophilic part of the hydrophobin.

It was checked with the aid of the coated silicon wafer by means of contact angle measurement whether the hydrophilic domain of the self-assembling protein and with it also the functional domain R5P is oriented toward the medium, i.e., on the side facing away from the silicon wafer. For this purpose, the contact angle in air was determined according to the sessile drop method (Drop Shape Analysis System DSA10, Krüss GmbH, Germany). The contact angle in degree of a drop of 2 µl of deionized water was determined. An uncoated silicon wafer cleaned with ethanol has a contact angle θ=35.2±2°. The silicon wafer coated with HFBI-(R5P)$_2$ had a contact angle θ=56.4±0.7°. This is clear evidence that the hydrophilic domain is exposed in the medium.

Example 7: Production of a Hydrophobin Bilayer on a Silicon Wafer

An ordered protein bilayer of a hydrophobin, as obtained in Example 1, was generated on a silicon wafer. For this purpose, the fusion protein HFBI-(R5P)$_2$ was used which contains a class I hydrophobin (HFBI from *Trichoderma reesei*) as a self-assembling domain and as a functional domain a mineralization tag.

First, for sedimentation of larger protein aggregates, a centrifugation (15 min at 18,000×g, 4° C.) was performed and the protein concentration was determined (according to Lowry). The sediment was discharged. A protein concentration of 100 ng/µl was adjusted.

To this protein-containing solution, a filtered 10 mM sodium sulfate solution (Na$_2$SO$_4$) was added in four portions during a time period of 10 min. Subsequently, an 8 mM solution of sodium dodecylsulfate (SDS) is added. For HFBI-(R5P)$_2$ the added salt concentration was 0.05 mM and the surfactant quantity per liter of the solution adjusted to a protein concentration of 100 ng/µl was 20 µmol so that a final surfactant concentration of 20 µmol/l was adjusted in the solution.

The stabilized solution obtained in this manner was clear.

The stabilized solution that contains multimers of the hydrophobin was used for coating a silicon wafer with edge lengths 1×1 cm. For this purpose, 200 µl of the stabilized protein-containing solution was applied to the silicon wafer with incubation for at least 30 min. Subsequently, the supernatant solution was drawn off and the silicon wafer coated with HFBI-(R5P)$_2$ washed in filtered, twice distilled water. The storage of the coated silicon wafer was done in the dialysis buffer mentioned in Example 1.

Subsequently, the drawn-off stabilized protein solution was used for further coating processes.

In order to accessible the functional domain of the self-assembling fusion protein on the substrate Example 8: Characterization of the Coating with HFBI-(R5P)$_2$ and HFBI-(XSR5P)$_3$ on a Silicon Wafer Produced in Example 6 by Means of Ellipsometry The coated silicon wafer obtained in Example 2 was examined ellipsometrically (Multiskop of the company OPTREL (Berlin)). The change of the polarization plane of a monochromatic laser beam (wavelength 632.8 nm) was determined by reflection at an angle of 136°. By measuring the intensity of the perpendicular (R$_S$) and parallel (R$_p$) reflected planes of incidence of the polarized light beam, the intensity ratio (ρ) was determined. The ellipsometric angles Δ and Ψ are derived by the FRENSEL equations. By including in the calculation the refractive indices of the single layers, the layer thickness of the uppermost layer was calculated.

$$\rho = \frac{R_p}{R_s} = \frac{|R_p|}{|R_s|} e^{i(\delta_p - \delta_s)} = \tan(\Psi) e^{i\Delta}$$

In this context, $\delta_p$ and $\delta_s$ indicate the phase difference to the zero point of light polarized perpendicular and in parallel. The optical constants known from the literature were used for silicon as a substrate and silicon dioxide. As an index of refraction of the protein film 1.375 was used.

The determined layer thickness of HFBI-(R5P)$_2$ on the silicon wafer amounted to 25.7±1.8 Å, respectively 25.8±0.8 Å for the construct HFBI-(XSR5P)$_3$. These layer thicknesses correspond to the literature values of a bilayer of the hydrophobin.

The following Table 3 shows the ellipsometric data of an analysis of seven different specimens (1 to Z), the different values in the individual rows were taken at different measuring points on the respective specimen):

TABLE 3

Ellipsometric measured data for substrates coated with HFBI-(R5P)$_2$

|  | 1 | 2 | 3 | 4 | 5 | 6 | Z |  |  |
|---|---|---|---|---|---|---|---|---|---|
| □$_{SiO2}$ [°] | 175.975 | 176.063 | 175.282 | 175.894 | 175.858 | 175.923 | 175.47 |  |  |
| d$_{SiO2}$ [nm] | 16 | 15.6 | 19.3 | 16.4 | 18.8 | 16.3 | 18.4 |  |  |
|  | 170.937 | 171.241 | 170.099 | 170.964 | 170.101 | 171.524 | 169.585 |  |  |
|  | 170.617 | 171.219 | 170.429 | 171.171 | 169.925 | 171.368 | 170.165 |  |  |
|  | 170.648 | 171.881 | 170.093 | 171.03 | 169.968 | 171.227 | 169.759 |  |  |
|  | 171.278 | 171.624 | 170.37 |  | 170.217 | 171.648 | 170.248 |  |  |
|  | 171.054 | 171.763 | 170.192 |  |  | 171.073 | 170.482 |  |  |
|  |  | 171.472 |  |  |  | 171.636 |  |  |  |
| □$_{protein}$ [°] | 170.907 | 171.533 | 170.237 | 171.055 | 169.998 | 171.413 | 170.048 |  | standard |
|  | 0.279 | 0.272 | 0.155 | 0.106 | 0.092 | 0.232 | 0.367 | average | deviation |
| D$_{protein}$ [nm] | 26.2 | 23.4 | 26 | 25 | 27.8 | 23.2 | 28 | 25.7 | ±1.8 |

Example 9: Determination of the Exposition of Functional Domains for Self-Assembling Fusion Proteins With the self-assembling fusion protein HFBI-(R5P)$_2$ produced in Example 1, a silicon wafer was coated with a bilayer of the protein analog to Example 7. The layer thickness which was determined ellipsometrically analog to Example 8 amounted to 25.7±1.8 Å. In the fusion protein the functional domain, the R5P subunit of the silaffin, is fused with the hydrophilic part of the hydrophobin.

It was checked with the aid of the coated silicon wafer by means of contact angle measurement whether the hydrophilic domain of the self-assembling protein and thus also the functional domain R5P is oriented toward the medium, i.e., on the side facing away from the silicon wafer. For this purpose, the contact angle in air was determined according to the sessile drop method (Drop Shape Analysis System DSA10, Krüss GmbH, Germany). The contact angle in degree of a drop of 2 µl of deionized water was determined.

An uncoated silicon wafer cleaned with ethanol had a contact angle θ=35.2±2°. The silicon wafer coated with HFBI-(R5P)$_2$ had a contact angle θ=54.1±0.9°. This is clear evidence that the hydrophilic domain is exposed in the medium.

to make, remaining surfactant was removed from the coated substrate by means of precipitation reaction.

Example 10: Examination of the Accessibility of the Fused HA Tag of a Silicon Wafer Coated with Ccg2-HA For determining the orientation of the deposited protein monomers on a silicon wafer coated with Ccg2-HA in analogy to Example 2, coupling of a fluorescence-marked antibody was carried out at the fused protein domain of a hydrophobin-fusion protein. For the fluorescence-microscopic analysis of the accessibility of the HA tag, the antibody anti-HA, AlexaFluor® 488 conjugate (INVITROGEN GMBH; Darmstadt, Germany) was diluted in accordance with manufacturer's instructions and incubated for 30 min on the substrate. Subsequently, the substrate was washed three times with twice distilled water in order to remove residues of unbonded antibody. Fluorescence-microscopic images were performed with a Zeiss Axio Observer.Z1 (CARL ZEISS MICROIMAGING GMBH; Jena, Germany) in combination with the corresponding filter set 38 GFP. A green fluorescing substrate surface confirms the accessibility of the fused HA tag.

As a reference, a substrate according to Example 2 was treated analogously with BSA. After incubation with the antibody anti-HA, AlexaFluor® 488 conjugate, no green fluorescing signals were detectable on the substrate surface.

Example 11: Examination of the Accessibility of a Fused Luciferase Tag of a Plastic Surface Coated with HFBI-GLuc For determining the accessibility of protein domains of a fusion protein, coating of a silicon wafer with HFBI-GLuc was carried out in analogy to Example 2. The fused luciferase domain (GLuc) catalyzes the chemical reaction of luciferin with emission of light at a wavelength of 475 nm. In addition to a visual evaluation, the quantitative fluorescence analysis was carried out by means of Infinite M200 plate reader (TECAN GROUP LTD.; Männedorf, Germany). The unfused protein domains (HFBI or GLuc) serve as references.

After the addition of luciferol, the bifunctional hydrophin chimera (HFB1-Gluc) as well as the subunit, as expected, showed a luminescence signal. The catalytically inactive HFB1 subunit does not show a luminescence signal. In a second experiment, the proteins were deposited on a polystyrene surface as in Example 2. Reaction buffer was overlaid onto the substrates and the reaction was initiated by the addition of luciferol. Exclusively the immobilized bifunctional hydrophin chimera showed a significant luminescence signal.

Example 12: Examination of the Long Term Stability of a Protein-Containing Coating Solution Containing Ccg2-tRFP or HFBI-tRFP In order to examine the effect of ionic surfactant on the surface activity of the self-assembling proteins, CTAB was added to fluorescing fusion proteins. The fluorescing fusion proteins consist of a hydrophobin (Ccg2 or HFBI) which constitutes the self-assembling domain and a red fluorescing peptide domain (tRFP). The red fluorescing peptide domain enables examination of the effect of ionic surfactants on the structure of the fusion protein by means of fluorescence measurement. A change in the fluorescence intensity permits direct conclusions on conformation changes of the protein scaffolding which are caused by interactions with the ionic surfactant.

Providing a protein-containing solution, containing a fusion protein (Ccg2-tRFP or HFBI-tRFP) or an unfused tRFP peptide sequence with the concentration 200 ng/µL, was added optionally in four portions a solution of ionic surfactants, containing CTAB, to a final concentration of ionic surfactant of 1 mM. Subsequently, all solutions were filtered through a filter (0.22 µm). The effect of the filtration, as well as the effect of added ionic surfactants was examined in the following for the time period of one week.

Due to the properties of self-assembling proteins, the filtration of the protein-containing solutions, containing exclusively the fusion protein (Ccg2-tRFP or HFBI-tRFP) without addition of ionic surfactant, led to a reduction of the fluorescence intensity by 37%0 or 46%. However, the protein-containing solution, containing exclusively unfused tRFP without addition of ionic surfactant, showed no drop in the fluorescence intensity. The fluorescence intensity was controlled in the following every 24 hours for a time period of one week. All samples showed a continuous drop in the fluorescence intensity. After one week, in all samples a fluorescence was detectable that was reduced by approx. 95% relative to the initial value.

The opposite result was obtained in case after addition of an ionic surfactant. The fluorescence intensity of the protein-containing solution, containing unfused tRFP peptide sequence and CTAB, dropped by 25%. The filtration of this sample had no effect on the fluorescence intensity. In case of the protein-containing solutions containing a fusion protein (Ccg2-tRFP or HFBI-tRFP), the addition of an ionic surfactant had no influence on the fluorescence intensity. Even after filtration of these solutions the fluorescence intensity remained unaffected. The fluorescence intensity was controlled in the following every 24 hours for a time period of one week. The protein-containing solutions, containing a fusion protein (Ccg2-tRFP or HFBI-tRFP) and an ionic surfactant, showed no drop in the fluorescence intensity across the entire testing period. The fluorescence intensity of the protein-containing solutions, containing keeping the unfused tRFP peptide sequence and an ionic surfactant, continuously dropped across the entire testing period. After one week, fluorescence was detectable in this sample that was reduced by about 67% relative to the initial value.

What is claimed is:

1. Method for coating a substrate with a monolayer or a bilayer of self-assembling proteins, selected from hydrophobins or surface layer proteins or recombinant fusion proteins with at least two domains, wherein at least one domain is a hydrophobin or a surface layer protein and one domain is a functional domain, the method comprising the steps:
   i. providing a protein-containing coating solution,
   ii. contacting the surface of the substrate with the protein-containing coating solution,
   iii. removing a supernatant solution from the coated substrate and/or drying the coated substrate,
   characterized in that the step of providing the protein-containing coating solution includes:
   a) separating aggregated protein units from an aqueous solution of self-assembling proteins so that a concentration of the self-assembling proteins in the aqueous solution after separation of the aggregated protein units amounts to at least 5 ng/µl, wherein the aqueous solution has a pH value of 7 to 9.5, and
   b) adding a solution of ionic surfactants in a range of 1 mmol/l to 10 mmol/l or in a range of 1 µmol/l to 500 µmol/l, the solution of ionic surfactants being added in portions, and
   c1) adding a salt-containing solution with bivalent metal ions or anions, wherein a concentration of the metal ions or anions in the aqueous solution amounts to 0.01 mmol/l to 10 mmol/l, or
   c2) adding bases or acids so that the pH value is shifted in a direction of the isoelectric point of the self-assembling proteins,
   to generate and stabilize monomers or oligomers of the self-assembling proteins in the protein-containing solution, wherein so much ionic surfactant is added that only the surface-active part of each active protein monomer or predominant protein oligomer is enveloped by surfactant particles.

2. Method according to claim 1, characterized in that the surfactants are selected from the group of hydrocarbon-coupled sulfates, sulfonates or carboxylates or from the group of quarternary ammonium compounds.

3. Method according to claim 1, characterized in that the salt-containing and/or alkaline and/or acidic solution contains alkaline earth metal ions or metal ions of the transition metal groups I and II in the form of chlorides, nitrates, carbonates, acetates, citrates, gluconates, hydroxides, lactates, sulfates, succinates or tartrates, or inorganic anions, in particular halides, hydroxides, nitrates, carbonates, sulfates, phosphates but also organic anions, in particular acetates, citrates, succinates or tartrates which have alkali metal ions as counter ions.

4. Protein-containing coating solution, containing monomers or oligomers of self-assembling proteins, selected from hydrophobins or surface layer proteins or recombinant fusion proteins with at least two domains, wherein at least one domain is hydrophobin or surface layer protein and one domain is a functional domain, wherein the surface-active part of the monomers or oligomers is enveloped by ionic surfactants, wherein the protein-containing coating solution is provided by:
   a) separating aggregated protein units from an aqueous solution of self-assembling proteins so that a concentration of the self-assembling proteins in the aqueous solution after separation of the aggregated protein units amounts to at least 5 ng/µl, wherein the aqueous solution has a pH value of 7 to 9.5, and
   b) adding a solution of ionic surfactants in a range of 1 mmol/l to 10 mmol/l or in a range of 1 µmol/l to 500 µmol/l, the solution of ionic surfactants being added in portions, and
   c1) adding a salt-containing solution with bivalent metal ions or anions, wherein a concentration of the metal ions or anions in the aqueous solution amounts to 0.01 mmol/l to 10 mmol/l, or
   c2) adding bases or acids so that the pH value is shifted in a direction of the isoelectric point of the self-assembling proteins,
   to generate and stabilize monomers or oligomers of the self-assembling proteins in the protein-containing coating solution, wherein so much ionic surfactant is added that only the surface-active part of each active protein monomer or predominant protein oligomer is enveloped by surfactant particles.

5. Use of a protein-containing coating solution according to claim 4 for coating substrate surfaces.

6. Substrate comprising a protein-containing coating of at least one self-assembling protein, characterized in that
   on the substrate surface a monolayer or a bilayer of self-assembling proteins, selected from recombinant fusion proteins with at least two domains, wherein at least one domain is a hydrophobin or a surface layer protein and one domain is a functional domain, is arranged,
   on the surface of the monolayer or of the bilayer of self-assembling proteins a layer which contains at least one ionic surfactant is present, wherein the surfactant is present in coordinative bond with the self-assembling protein,
   wherein the functional domain is arranged on the side of the protein-containing coating that is facing away from the substrate.

7. Substrate according to claim 6, characterized in that the functional domain is a fluorescent protein domain, a catalytic domain, or a protein domain with enzyme activity.

* * * * *